(12) United States Patent
Björling et al.

(10) Patent No.: US 8,755,874 B2
(45) Date of Patent: Jun. 17, 2014

(54) IMPLANTABLE MEDICAL DEVICE AND METHOD FOR CLASSIFYING ARRHYTHMIA EVENTS

(75) Inventors: Anders Björling, Solna (SE); Rupinder Bharmi, Canyon County, CA (US); Michael Broomé, Ekerö (SE); Karin Järverud, Solna (SE)

(73) Assignee: St. Jude Medical AB, Jarfalla (SE)

( * ) Notice: Subject to any disclaimer, the term of this patent is extended or adjusted under 35 U.S.C. 154(b) by 288 days.

(21) Appl. No.: 12/989,581

(22) PCT Filed: May 7, 2008

(86) PCT No.: PCT/SE2008/000312
§ 371 (c)(1),
(2), (4) Date: Jan. 6, 2011

(87) PCT Pub. No.: WO2009/136817
PCT Pub. Date: Nov. 12, 2009

(65) Prior Publication Data
US 2011/0112419 A1   May 12, 2011

(51) Int. Cl.
*A61B 5/04*       (2006.01)
(52) U.S. Cl.
USPC ............... 600/513; 607/17; 607/18; 607/19; 600/515; 600/516; 600/517; 600/518
(58) Field of Classification Search
USPC ................. 607/17–19; 600/515–518, 513
See application file for complete search history.

(56) References Cited

U.S. PATENT DOCUMENTS

| | | |
|---|---|---|
| 5,042,497 A | 8/1991 | Shapland |
| 5,370,667 A | 12/1994 | Alt |
| 6,600,949 B1 | 7/2003 | Turcott |
| 6,813,514 B1 | 11/2004 | Kroll et al. |
| 7,149,569 B1 | 12/2006 | Fain |
| 7,200,440 B2 | 4/2007 | Kim et al. |
| 7,206,633 B2 | 4/2007 | Saba |
| 7,308,309 B1 | 12/2007 | Koh |
| 7,435,221 B1 | 10/2008 | Bharmari |
| 2004/0230129 A1 | 11/2004 | Haefner |
| 2005/0154421 A1 | 7/2005 | Ousdigian |
| 2006/0178704 A1 | 8/2006 | Elahi et al. |
| 2007/0112276 A1 | 5/2007 | Simms, Jr. |
| 2007/0149890 A1 | 6/2007 | Li et al. |
| 2007/0179386 A1 | 8/2007 | Michard et al. |
| 2007/0238939 A1 | 10/2007 | Giftakis et al. |
| 2007/0239053 A1 | 10/2007 | Bhunia |

OTHER PUBLICATIONS

Supplementary EP Search Report, dated Sep. 18, 2012—EP Application No. 08767036.0.

*Primary Examiner* — Michael Kahelin
*Assistant Examiner* — Mallika D Fairchild

(57) ABSTRACT

In an implantable medical device such as an implantable cardiac defibrillator, and a method for classifying arrhythmia events, IEGM signals are analyzed to detect an arrhythmia event and a respiratory pattern of the patient is sensed. At least one respiratory parameter reflecting characteristics of the respiratory pattern of the patient is determined based on the sensed respiratory pattern and a respiratory measure corresponding to a change of a rate of change of the at least one respiratory parameter is calculated. The detected arrhythmia event is classified based on the respiratory measure and the IEGM signals, wherein arrhythmia events that satisfy at least a first criterion is classified as an arrhythmia event requiring therapy.

12 Claims, 5 Drawing Sheets

IMPLANTABLE MEDICAL DEVICE AND METHOD FOR CLASSIFYING ARRHYTHMIA EVENTS

BACKGROUND OF THE INVENTION

1. Field of the Invention

The present invention generally relates to the field of implantable devices. More specifically, the present invention relates to an implantable medical device, for example, an implantable cardiac defibrillator for the identification of arrhythmias and the discrimination between non-lethal arrhythmias and lethal arrhythmias that may or may not require therapy.

2. Description of the Prior Art

Identifying an arrhythmia based on its intracardiac electrogram is a commonly used technique in, for example, implantable cardiac defibrillators (ICD), which are designed to deliver therapy for life-threatening ventricular arrhythmias. The heart rate is measured by detecting R waves in the IEGM originating from the ventricle using a ventricular lead. If the rate is higher than a specific limit, it is an indication that a tachycardia is present. A defibrillator is capable of delivering a high-energy electrical stimulus via medical leads to the heart that is sometimes referred to as defibrillation shocks. The shock interrupts a fibrillation, allowing the heart to re-establish a normal rhythm for efficient pumping of blood. The defibrillator is able to sense cardiac signals deliver therapy to heart based on such signals. However, a problem often encountered in these implantable cardiac defibrillators is that shocks are delivered inappropriately for e.g. supraventricular tachycardias. In fact, studies do indicate that roughly 20-30% of all delivered ICD shocks are inappropriate. About 16% of patients receive inappropriate therapies (single of multiple). It has further been found that patients experience 1.6 to 1.8 inappropriate shocks per year. One major reason for this delivery of inappropriate shock is the limited accuracy of the defibrillator in the discrimination between a truly life-threatening ventricular arrhythmia and a supraventricular tachycardia, which often causes similar electrical activity patterns, i.e. similar intracardiac electrograms. These inappropriate delivered shocks constitute a significant source of physical and emotional stress and discomfort for the patient. Further, the shocks also cause unnecessary consumption of the device battery, which shorten the life of the device.

Therefore, ICDs of today often use different complementary discrimination techniques. For example, the interval stability is a parameter that may be used to improve the discrimination since VTs (ventricular tachycardia) tend to be more stable in rate than SVTs (supraventricular tachycardias). Another parameter is atrial-ventricular event association. During sinus tachycardias (i.e. benign tachycardias caused e.g. of high physical activity) shows atrial-ventricular event association, e.g. each P wave is followed by an R wave. In case of VTs, the atrial and ventricular events are disassociated. Morphology analysis may also be used since it has been shown that the IEGM during a VT is different from that of a normal heart beat. SVTs give in most cases a rise to the normal morphology.\

A number of attempts have also been made within the prior art to overcome this problem.

For example, in U.S. Pat. No. 7,206,633 a device and method for identification and detection of abnormal heart rhythm occurring in either the supraventricular or ventricular cardiac regions and in particular a device and method for discriminating between supraventricular tachycardia and ventricular arrhythmia. The technique according to U.S. Pat. No. 7,206,633 is based on intracardiac electrograms recorded by atrial and ventricular sensing leads that distinguish their temporal relationships following tachycardia recurrence subsequent to a train of simultaneous anti-tachycardia pacing (ATP) bursts in the atria and ventricles.

In US 2005/0154421 an implantable medical device for identifying suspected non-lethal or lethal arrhythmias is shown. The device takes actions to avoid or delay delivery of a defibrillation shock in case of a non-lethal arrhythmia and respiration rate, respiration depth, and/or activity level is used to discriminate between lethal and non-lethal arrhythmia. Impedance measured over the thoracic region of the patient can be used to calculate the respiration rate and respiration depth. Thus, in US 2005/0154421, the respiratory pattern and/or activity level are used as additional input to the analysis of the intracardiac electrograms in the discrimination between non-lethal and lethal arrhythmias.

Furthermore, in U.S. Pat. No. 5,042,497 an implantable medical device capable of predicting and preventing cardiac arrhythmias is disclosed. The device monitors both ECG signals and autonomic neural tone signals. If both these signals indicate arrhythmia preventive or curative actions are taken by the device. Arrhythmias are characterized by increased sympathetic activity. This sympathetic activity can be followed by monitoring, among other, the respiration rate variability of the patient. According to U.S. Pat. No. 5,042, 497, a decrease in variability of respiration rate indicate elevated sympathetic activity and thereby arrhythmia. The variability in respiration rate is determined on basis on the interval between consecutive breaths of the patient.

In U.S. Pat. No. 5,370,667 an implantable medical device that provides electrical therapy to a heart of a patient in order to treat pathological tachycardia is disclosed. The device has a first sensor that generates a signal indicative of the patient's ECG. A second sensor is an activity sensor that generates a signal representative of the current status of physical activity by the patient. For example, the impedance over the chest is measured to indicate the activity of the patient. The readings of the first sensor (activity) sensor are employed for dynamically adjusting the arrhythmia threshold used, together with the ECG signal, for detecting the presence of arrhythmia. The device utilizes different arrhythmia thresholds depending on the patient activity but the detection of the arrhythmia condition is performed solely based on ECG signals.

Consequently, a number of prior art solutions utilize breathing pattern as an additional parameter to the ECG signals to improve and increase the accuracy in the discrimination between lethal and non-lethal arrhythmias in order to reduce the number of erroneously delivered defibrillation shocks. However, there is still a need within the art of improved devices and method that are capable of discriminating between lethal and non-lethal arrhythmias with a higher degree of accuracy in order to further reduce the number of inappropriate delivered defibrillation shocks. As discussed above, such an improved device and method that is capable of reducing or even avoid inappropriate shock would have beneficial effect on the physical and emotional state of patients with defibrillators as well as reduce the cost of health care of the society.

SUMMARY OF THE INVENTION

Thus, an object of the present invention is to provide an improved implantable medical device and a method for such a device that are capable of discriminating between arrhythmias requiring therapy and arrhythmias that do not require therapy with a high degree of accuracy.

A further object of the present invention is to provide an improved implantable medical device and a method for such a device that are capable of classifying arrhythmias depending on whether therapy is required or not with a high degree of accuracy.

Another object of the present invention is to provide an improved implantable medical device and a method for such a device that are capable of substantially preventing misinterpretations of the cardiac electrical signals with regard to arrhythmias and to substantially avoid the delivery of inappropriate shocks.

According to a first aspect of the present invention, an implantable medical device for classifying arrhythmia events is connectable to at least one medical lead adapted to be placed at or within a heart of a patient. The medical lead includes at least one electrode adapted to sense electrical activity of the heart and to produce at least one signal representative of the electrical activity. The medical device includes an IEGM analyzing circuit adapted receive the signal representative of the electrical activity and to analyze IEGMs of the heart to detect an arrhythmia event. The medical device further has a sensing circuit adapted to sense a respiratory pattern of the patient and to produce at least one signal representative of the respiratory pattern. A respiratory parameter determining circuit determines at least one respiratory parameter representing characteristics of the respiratory pattern of the patient based on the sensed respiratory pattern and determines a respiratory measure corresponding to a change of a rate of change of the at least one respiratory parameter. An arrhythmia classifying circuit classifies the detected arrhythmia event based on the respiratory measure and the analysis of the IEGM signals. Arrhythmia events that satisfy at least a first criterion are classified as an arrhythmia event requiring therapy.

According to second aspect of the present invention, a method is provided for classifying arrhythmia events in an implantable medical device being connectable to at least one medical lead adapted to be placed at or within a heart of a patient. The medical lead includes at least one electrode adapted to sense electrical activity of the heart and to produce at least one signal representative of the electrical activity. The method includes the steps:

analyzing IEGMs of the heart to detect an arrhythmia event;

sensing a respiratory pattern of the patient producing at least one signal representative of the respiratory pattern;

determining at least one respiratory parameter reflecting characteristics of the respiratory pattern of the patient based on the sensed respiratory pattern;

determining a respiratory measure corresponding to a change of a rate of change of the at least one respiratory parameter; and classifying the detected arrhythmia event based on the respiratory measure and the analysis of the IEGM signals, wherein arrhythmia events that satisfy at least a first criterion is classified as an arrhythmia event requiring therapy.

The present invention is based on the finding that the time of onset of a change in the respiratory pattern or the changing rate of the respiratory pattern change is an early and accurate indication of a lethal arrhythmia and therefore is a better parameter to use in the discrimination between lethal and non-lethal arrhythmias, i.e. between arrhythmias requiring therapy and arrhythmias that do not require immediate therapy, than simply the actual change of the respiratory pattern. Thus, this information is used in combination with the IEGM data to determine whether a high rate is unstable (i.e. causes a low arterial pressure) and should be treated, for example, shocked, or a stable (i.e. the heart still manages to uphold a high arterial pressure) and should be treated with ATP or not at all. In connection with this, it has been found that the change of a rate of change of the respiratory frequency and/or the tidal volume is respiratory parameters containing valuable respiratory information for the discrimination. An unstable tachycardia causes lack of oxygen to the brain. This triggers a sympathetic activation which e.g. increases the respiratory drive. Since a stable tachycardia does not cause a lack of oxygen to the brain, the sympathetic response is not triggered and the respiratory pattern is not affected.

The respiratory components or parameters, e.g. the tidal volume and the respiratory frequency, can be determined by means of the cardiac impedance of the patient, which is indicative of the respiratory pattern of the patient. By measuring, for example, the impedance between the case of the implantable medical device and electrodes placed in the ventricle, for example, a tip electrode of a medical lead connectable to the device, an impedance signal that varies in connection with, inter alia, the respiration can be acquired.

According to another embodiment of the present invention, the IEGMs may be used to determine the respiratory pattern parameters.

In yet another embodiment, a left atrial pressure (LAP) sensor is arranged in left atrium LA, and the average LAP, which will vary with inspiration and expiration, may be used by the respiratory parameter to estimate the tidal volume and/or respiratory frequency.

During a hemodynamically compromising VT, the respiratory frequency may increase, the tidal volume may increase or both entities may increase. The respiratory measure in accordance with the present invention, may take one of this parameters or both parameters into account. In one specific embodiment, a measure incorporating both parameters is utilized. Thus, to be able to detect the changes in respiratory drive using only a single measure, this measure must take both tidal volume and respiratory frequency into account. For example, the product of the two parameters can be calculated, a measure that correlates to the minute ventilation (the minute ventilation represents the amount of oxygen delivered to the body per minute). In another alternative, the respiratory measure is set to a linear combination of the frequency and the tidal volume estimate. Assigning different weights to the frequency and the tidal volume estimate, the importance of them can be different. Thus, if it is seen that the respiratory frequency changes more often as a cause of a VT requiring therapy than does the tidal volume, the respiratory frequency would have a higher weight than the tidal volume.

In a further alternative, the rate of change of the change of the respiratory parameter, e.g. the weighted combination of the tidal volume and the respiratory frequency, is calculated to obtain the respiratory measure, for example, by calculating the second derivative of the respiratory parameter. However, as the skilled person realizes, another alternative may be to calculate the respiratory measure by determining the tidal volume and the respiratory frequency individually and determine a weighted combination of the change of rate of changes.

According to an embodiment of the present invention, the arrhythmia classifying circuit is adapted to determine the at least first criterion to be satisfied if the respiratory measure, i.e. the change of the rate of change, is higher than a predetermined threshold value. Thereby, it is possible to improve the discrimination since only arrhythmias being correlated with a sufficiently high rate of change (i.e. that exceeds the predetermined limit) of the respiratory measure are classified as arrhythmias requiring therapy.

In a further embodiment of the present invention, the arrhythmia classifying circuit is adapted to upon receiving information from the arrhythmia detection circuit that an arrhythmia event has been detected, monitor the respiratory measure, compare the time points for the respective onset of the detected arrhythmia event and of a respiratory measure being higher than the predetermined threshold; and determine the at least first criterion to be satisfied if the respiratory measure is higher than a predetermined threshold value and an onset of the change occur within a predetermined period of time from the onset of the detected arrhythmia event.

Thereby, it is possible to further improve the discrimination since only arrhythmias correlated with a sudden and sufficiently high rate of change (i.e. that exceeds the predetermined limit) of the respiratory measure is classified as arrhythmias requiring therapy.

According to an exemplary embodiment of the present invention, the implantable medical device includes an impedance measuring circuit adapted to, during impedance measuring sessions, measure at least one impedance signal between at least a first pair of electrodes being connectable to the implantable medical device, the electrodes being located such that measured impedance signals substantially reflects the respiratory pattern of the patient; and wherein the respiratory parameter determining circuit is adapted to determine the at least one respiratory parameter based on the measured impedance signals.

In a further embodiment of the present invention, the implantable medical device has an activity sensor adapted to sense a level of physiological activity the patient and to produce a signal representative of a current status of the physiological activity the patient; and the arrhythmia classifying circuit is adapted to determine that the at least one first criterion is not satisfied if an activity level of the patient is above a predetermined level. Thereby, it is possible to further improve the discrimination since arrhythmias correlated with a increase of the respiratory frequency and/or tidal volume caused by physical activity are ruled out as arrhythmias requiring therapy.

The arrhythmia classifying circuit can be adapted to classify an arrhythmia event that satisfies at least the first criterion as an arrhythmia event requiring shock treatment and to classify an arrhythmia event that satisfies at least a second criterion as an arrhythmia event requiring anti-arrhythmia pacing. Thus, the arrhythmias are classified in three groups. A first group including arrhythmias requiring therapy by means of a defibrillation shock (-s), a second group including arrhythmias requiring therapy by means of anti-arrhythmia pacing stimuli, and a third group including arrhythmias determined not to require therapy. An arrhythmia event that satisfies at least a first criterion may be classified as an arrhythmia event requiring shock treatment, an arrhythmia event that satisfies at least a second criterion may be classified as an arrhythmia event requiring anti-arrhythmia pacing (ATP), and an arrhythmia event that satisfied at least a third criterion may be classified as an arrhythmia event that do not require any therapy. For example, the first criterion may be the predetermined limit which in this embodiment corresponds to a significant impact on the respiration, i.e. a sudden increase of the rate of change of the respiratory frequency and/or tidal volume being above a predetermine limit, and an IEGM based determination that indicates that the arrhythmia event is a ventricular tachycardia (VT) or ventricular fibrillation (VF). Further, the second criterion may include a small (or in certain cases no) impact on the respiration, i.e. an increase of the rate of change of the respiratory frequency and/or tidal volume being above a lower predetermine limit but below the predetermined limit indicating shock therapy, and an IEGM based determination that indicates that the arrhythmia event is a ventricular tachycardia (VT). A third criterion may include no impact on the respiration, i.e. an increase of the rate of change of the respiratory frequency and/or tidal volume being below the lower predetermine limit indicating ATP, and, optionally, a determination that the activity level has changed.

In another embodiment of the present invention, a sudden decrease of the respiratory frequency and/or the tidal volume to a very low value near zero is an indication of apnea. This in combination with a detected event similar to total circulatory collapse, for example, a detected ventricular fibrillation is a clear indication that an arrhythmia requiring therapy by means of shock therapy has occurred.

As will be apparent to those skilled in the art, steps of the methods according to the present invention, as well as preferred embodiments thereof, are suitable to realize as computer program or as a computer readable medium.

DESCRIPTION OF THE PREFERRED EMBODIMENTS

The following is a description of exemplifying embodiments in accordance with the present invention. This description is not to be taken in limiting sense, but is made merely for the purposes of describing the general principles of the invention. Thus, even though particular types of implantable medical devices such as implantable cardioverter defibrillators (ICDs) will be described, the invention is also applicable to cardiac stimulators such as biventricular pacemakers, dual chamber stimulators, etc. Moreover, the invention is applicable to cardiac stimulators such as biventricular pacemakers, dual chamber stimulators, etc. including a defibrillator element.

Figure 1:
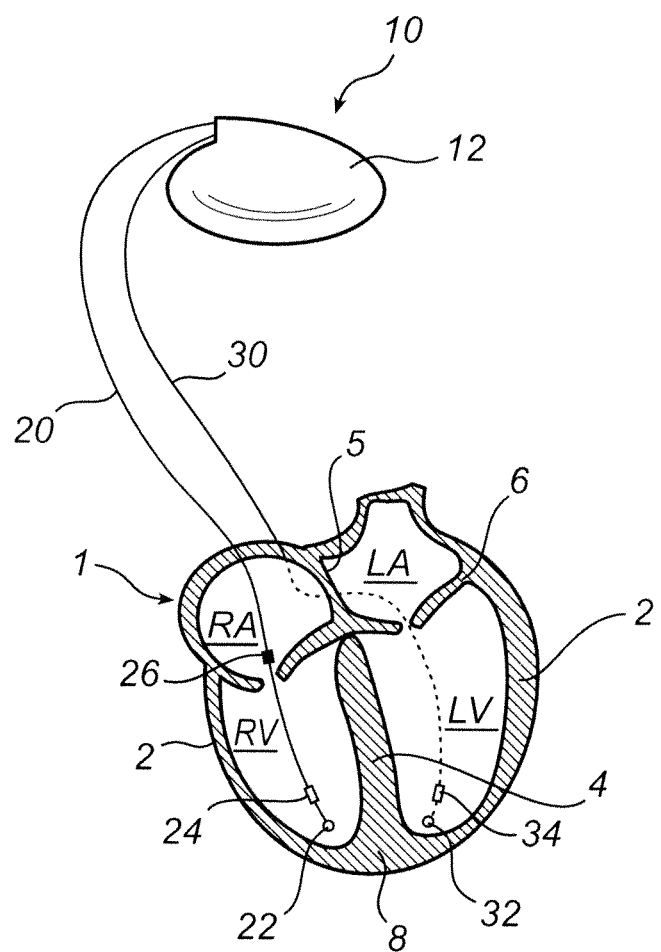
FIG. 1 is a schematic drawing of an exemplary human heart showing a configuration of one embodiment of an implantable medical device in accordance with the present invention.

With reference first to FIG. 1, there is shown an implantable medical device for classifying arrhythmias according to an embodiment of the present invention. According to this embodiment, the invention is implemented in an implantable cardiac defibrillator 10 even though, as indicated above, the invention can be implemented in a pacemaker, for example, a dual chamber stimulator.

The implantable medical device 10 is implanted in a surgically formed pocket in the flesh of the patient's chest (not shown), or other desired location within the body. A pace pulse generator (see FIG. 2), a control circuit (see FIG. 2) are included in the implantable medical device 10, which are housed in a case (can) 14 compatible with the tissue and fluids of the body (i.e. biocompatible). The control circuit (see FIG. 2) of the implantable medical device 10 is micro-processor based and includes memory, logic and other components to provide processing, evaluation and other functions necessary to determine, select and deliver appropriate therapy including electrical defibrillation and pulses of different energy levels and timing for ventricular defibrillation and pacing to the patient's heart 1 in response to an identified ventricular arrhythmia, which will be described in more detail below with reference to FIG. 2. The illustrated portions of the heart 1 include right atrium RA, the right ventricle RV, the left atrium LA, the left ventricle LV, cardiac walls 2, the ventricle septum 4, the valve plane 6, and the apex 8.

Implantable medical leads 20, 30 are connectable to the implantable medical device 10. The medical leads 20, 30 include distally located electrodes coupled at the proximal end to the signal generator 12 through an electrical connector in a header (not shown) of the case 14. The case 14 itself may be used as an electrode such as electrical ground, for sensing pacing, or defibrillation.

Thus, the implantable medical device according to the present invention in electrical communication with a patient's heart 1 by way of medical leads 20, 30. The implantable right ventricular lead 20 may have an atrial electrode 26 (e.g. a ring electrode), a ventricular tip electrode 22 and a ventricular annular or ring electrode 24. Thereby, right ventricular and atrial cardiac signals can be sensed and therapy can be delivered to the right ventricle RV. Furthermore, a "coronary sinus" lead 30 designed for placement via the coronary sinus in veins located distally thereof is connectable to the implantable medical device 10. For example, a distal tip electrode 32 and/or a distal ring electrode 34 can be placed adjacent to the left ventricle. Further, an electrode (not shown) can be placed adjacent to the right atrium RA. Thereby, left atrium and ventricular cardiac signals can be obtained and pacing therapy for the left ventricle LV can be delivered. Active or passive fixation of the leads may be used to assure suitable excitation and/or measurements.

According to this illustrated embodiment of the present invention, the atrial electrode 26 and the ventricular electrode 24 are positioned for use as defibrillation electrodes as well as for sensing in the atrial and ventricle, respectively. For defibrillation, the electrodes 26, 24 may cooperate with the case 12. A pericardial lead (not shown) including electrodes may also be connectable to the implantable medical device 10 and in such a case, the electrodes 26, 24 may cooperate with pericardially located electrodes. As the skilled person realizes, there are a number of other conceivable defibrillator implementations that may be used.

Figure 2:
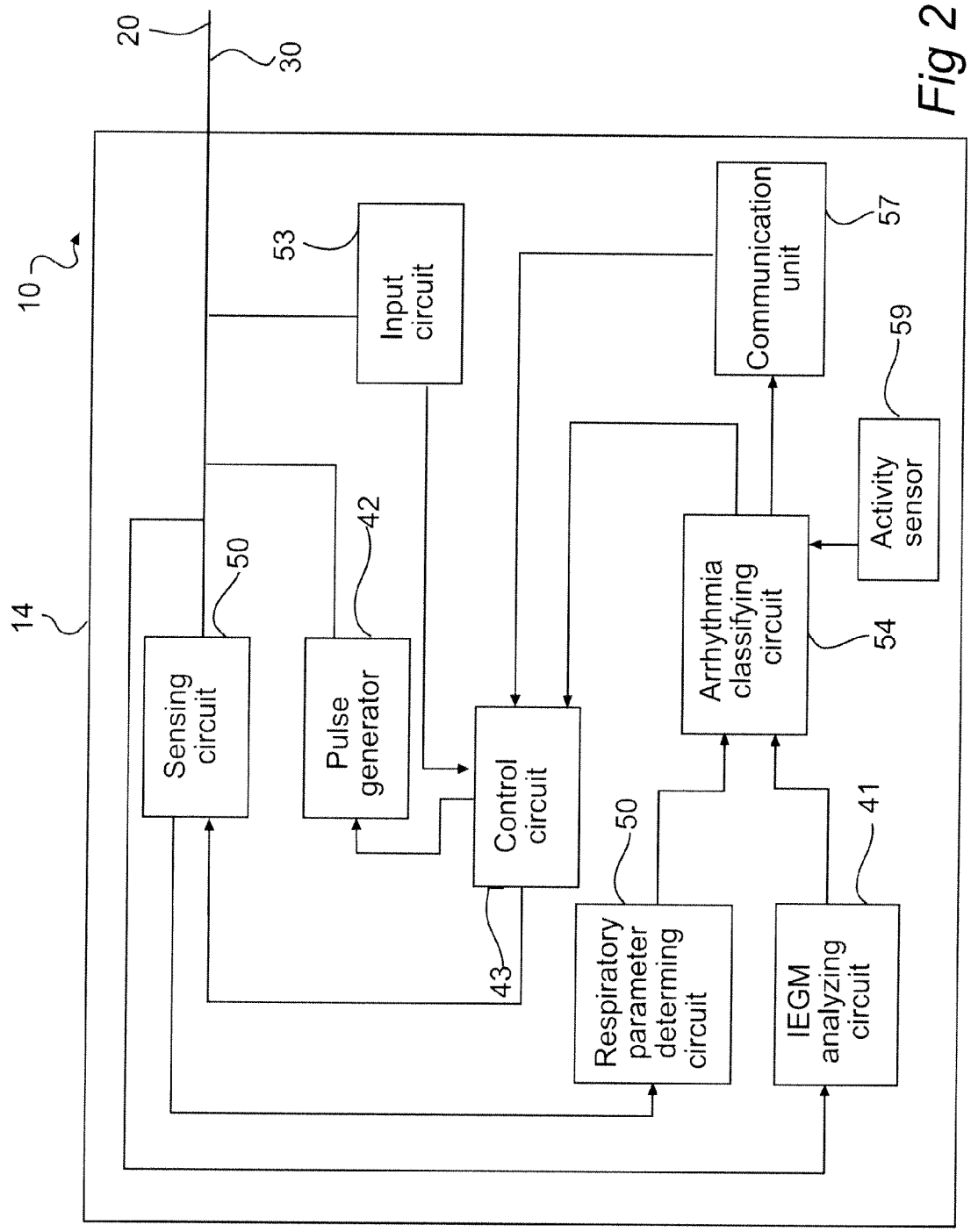
FIG. 2 is an illustration in a block diagram form of an implantable stimulator according to the embodiment shown in FIG. 1.

Turning now to FIG. 2, the defibrillator 10 of FIG. 1 is shown in a block diagram form. For illustrative purposes, reference is made to FIG. 1 for the elements of the leads that are intended for positioning in or at the heart.

An embodiment of the implantable medical device according to the present invention will be shown. The implantable medical device 10 has a housing 14 being hermetically sealed and biologically inert, see FIG. 1. Normally, the housing is conductive and may, thus, serve as an electrode. One or more pacemaker leads, where only two are shown in FIGS. 1, 20 and 30, are electrically coupled to the implantable medical device 10 in a conventional manner. The leads 20, 30 extend into the heart (see FIG. 1) via a vein of the patient. It is understood that the line indicated by the reference numerals 20, 30 in this case represent the two medical leads 20, 30 of FIG. 1. Further, more than two medical leads may be connected to the implantable medical device 10, in which case the line indicated by 20, 30 will represent more than two leads.

As discussed above with reference to FIG. 1, the leads 20, 30 comprise one or more electrodes, such a tip electrodes or a ring electrodes, arranged to, inter alia, transmit defibrillation shocks, pacing pulses for causing depolarization of cardiac tissue adjacent to the electrode(-s) generated by a pace pulse generator 42 under influence of a control circuit 43 comprising a microprocessor. The control circuit 43 may control, inter alia, pace pulse parameters such as output voltage and pulse duration and memory, which memory may include a random access memory (RAM) and/or a non-volatile memory such as a read-only memory (ROM). Detected signals from the patient's heart are processed in an input circuit 45 and are forwarded to the microprocessor of the control circuit 43 for use in logic timing determination in known manner.

Furthermore, the implantable medical device 10 for classifying arrhythmia events comprises an IEGM analyzing circuit 41 adapted to receive signals representative of the electrical activity from electrodes arranged in the medical leads 20, 30, and to analyse IEGMs of the heart 1 to detect an arrhythmia event. The arrhythmia detection can be performed in accordance with conventional manner. For example, the heart rate can be determined by detecting R waves in the IEGMs originating from the ventricle. If the rate is higher than a predetermined limit, this is an indication that a tachycardia is present.

Moreover, the implantable medical device 10 includes a sensing circuit 50 adapted to sense a respiratory pattern of the patient and to produce at least one signal representative of the respiratory pattern and a respiratory parameter determining circuit 52 adapted to determine at least one respiratory parameter reflecting characteristics of the respiratory pattern of the patient based on the sensed respiratory pattern. The respiratory parameter determining circuit 52 is further adapted to determine a respiratory measure corresponding to a change of a rate of change of the at least one respiratory parameter. It has been found by the inventors that the respiratory frequency and the tidal volume (i.e. the size of a breath) and, in particular, the time of onset of a or the change of the change of the respiratory frequency or tidal volume are particularly good discrimination parameters in that they constitute an early and accurate indication of a lethal arrhythmia.

According to one embodiment of the present invention, the sensing circuit is an impedance measuring unit adapted to carry out impedance measurements of the cardiac impedance of the patient indicative of the respiratory pattern of the patient. Now referring to FIG. 1, the respiratory pattern can be determined, by measuring, for example, the impedance between the case 12 and electrodes placed in the ventricle, for example, the tip electrode 22 or the ring electrode 24 whereby an impedance signal that varies in connection with, inter alia, the respiration can be obtained. Air has a high impedance compared to tissue and, hence, inspiration causes the impedance signal to rise. Similarly, expiration causes the impedance to drop. In this embodiment, the respiratory parameter determining circuit 52 may be adapted to calculate how often the impedance signal crosses a moving average of the impedance signal. Thereby, the respiratory frequency can be estimated. By counting how often a peak or trough occurs within a moving average window is also an alternative. Further alternatives for estimating respiratory frequency include FFT (fast Fourier transform) or Hilbert transform.

To estimate the tidal volume, for example, the peak-to-peak value of the impedance signal in a moving window (e.g. a few seconds wide) can be studied. This estimation will provide a relative measure.

Due to the influence of the cardiac activity, the measure impedance signal is preferably filtered using a low pass filter, for example, a filter having a limiting frequency of about 2.5 Hz before the actual analysis of the signal is performed.

According to another embodiment of the present invention, the IEGMs may be used to determine the respiratory pattern and in this case. For example, there is a baseline drift in the IEGM caused by the respiratory. This baseline drift is unwanted in cardiac event detection and is usually blocked our or attenuated by filtering. However, the respiratory parameter determining circuit 52 may be adapted to utilize this drift in that the IEGM signal is processed such that a more pronounced respiratory artefact is obtained. This artefact can then be processed in similar way as the impedance signal to acquire estimates of the tidal volume and/or the respiratory frequency. In case of ventricular IEGMs, the amplitude of the R waves (which varies with the respiratory cycle) can be assessed to estimate the tidal volume and the respiratory frequency.

In yet another embodiment, a left atrial pressure (LAP) sensor is arranged in left atrium LA, for example, by entering from right atrium, puncturing septum and attaching the sensor to wall in the left atrium. The average LAP will vary with inspiration and expiration and this signal may be used by the respiratory parameter determining circuit 52 to estimate the tidal volume and/or respiratory frequency.

During a hemodynamically compromising VT, the respiratory frequency may increase, the tidal volume may increase or both entities may increase. The respiratory measure in accordance with the present invention, may take one of this parameters or both parameters into account. In one specific embodiment, a measure incorporating both parameters is utilized. Thus, to be able to detect the changes in respiratory drive using only a single measure, this measure must take both tidal volume and respiratory frequency into account. According to embodiments of the present invention, the respiratory parameter determining circuit 52 calculates the product of the two parameters. This correlates to the minute ventilation, which represents the amount of oxygen delivered to the body per minute. In another alternative, the respiratory parameter determining circuit 52 sets the respiratory measure to a linear combination of the frequency and the tidal volume estimate. Assigning different weights to the frequency and the tidal volume estimate, the importance of them can be different. Thus, if it is seen that the respiratory frequency changes more often as a cause of a VT requiring therapy than does the tidal volume, the respiratory frequency would have a higher weight than the tidal volume.

Further, the respiratory parameter determining circuit 52 calculates the change of the rate of change of the respiratory parameter, e.g. the weighted combination of the tidal volume and the respiratory frequency, to obtain the respiratory measure by calculating the second derivative of the respiratory parameter. However, as the skilled person realizes, the respiratory parameter determining circuit 52 may in another alternative calculate the change of the rate of the change of the tidal volume and the respiratory frequency individually and calculate a weighted combination of the change of the rate of changes.

The implantable medical device 10 further comprises an arrhythmia classifying circuit 54 adapted to classify a detected arrhythmia event based on the calculated respiratory measure, wherein arrhythmia events that satisfy at least a first criterion is classified as an arrhythmia event requiring therapy.

Additionally, the implantable medical device 10 comprises a communication circuit 57, for example, an RF telemetry circuitry for providing RF communications including a transmitter and a receiver connected to an antenna. Thereby, for example, data contained in the memory of the control circuit 43 can be transferred to, for example, an external programmer device. Moreover, arrhythmia information can be transferred, via the communication circuit 57 and a wireless communication network, to a physician of the patient, for example, to a work station located at a hospital or care institution. Thus, the physician may be informed of the status of the patient and can be updated of the status at regular intervals or when an arrhythmia requiring therapy has occurred. The patient may also be provided with arrhythmia information. For example, an information message may be sent, via the communication circuit 57, to a work station located at the patient's home or a cellular phone of the patient, or a PDA (personal digital assistant), or a laptop computer, or a home monitoring device. The information message may inform the user, e.g. the patient, of the device receiving the message of the present status of the patient, for example, that an arrhythmia has been detected but that no therapy was required. A physician using an extracorporeal programmer can also communicate with the implantable medical device 10 and thereby obtain information on identified conditions and also reprogram the different functions of the implantable medical device 10.

In one embodiment, the implantable medical device includes an activity sensor 59 adapted to sense a level of physiological activity the patient and to produce a signal representative of a current status of the physiological activity patient. The activity sensor may be an accelerometer of conventional type. The arrhythmia classifying circuit 54 may be adapted to determine that the at least one first criterion is not satisfied if an activity level of the patient is above a predetermined level. Physical activity increases both the respiratory frequency and the tidal volume but the respiratory drive do not come as fast as in case of an arrhythmia. Using also the physical activity as a discrimination parameter, the specificity of the arrhythmia classification can be increased.

Figure 3:
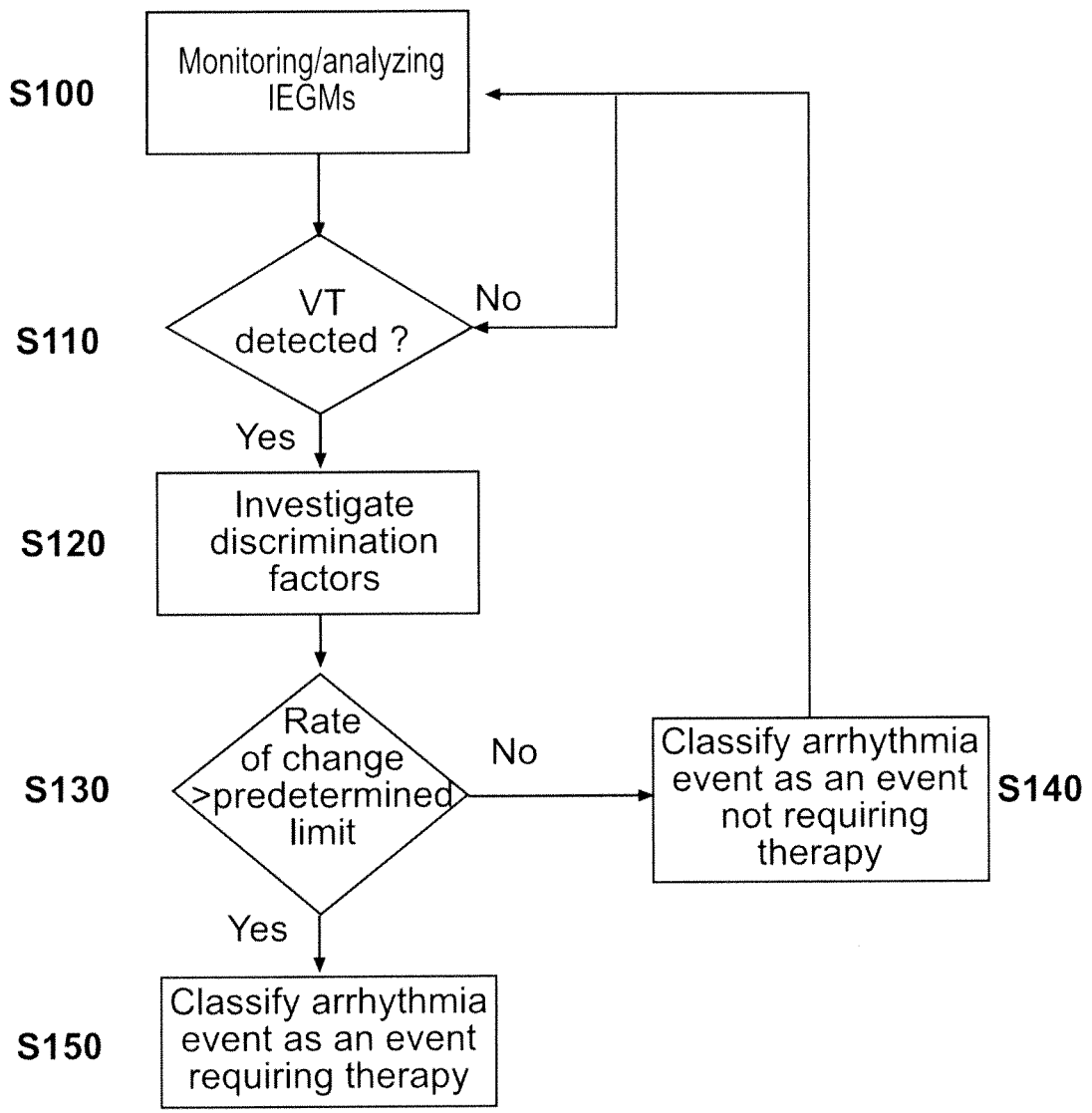
FIG. 3 is a flow chart describing the general principles of the method of the present invention.

Turning now to FIG. 3, the principles of the method for classifying a ventricular arrhythmia according to the present invention will be described. First, at step S100, IEGMs of the heart, i.e. electrical activity of the heart, are analyzed to detect a ventricular arrhythmia event, which may a continuous procedure. The acquired IEGMs are monitored and analysed in order to detect arrhythmias, for example, the heart rate may be measured by detecting R waves in the IEGMs originating from the ventricle. If the measured rate is higher than a specific predetermined limit, it is an indication that a tachycardia is present. Hence, in step S110, it is determined whether a ventricular arrhythmia event has been detected on not. If no, the procedure returns to step S100. On the other hand, if yes, the procedure proceeds to step S120 where additional discrimination factors are investigated. According to one embodiment, the respiratory pattern is investigated and respiratory measure corresponding to a change of a rate of change of at least one respiratory parameter reflecting characteristics of the respiratory pattern of the patient is determined. As discussed above, the respiratory frequency and/or the tidal volume (i.e. the size of a breath) and, in particular, the time of onset or a change of a change of the respiratory frequency and/or tidal volume have been found to be particularly good discrimination parameters in that they constitute an early and accurate indication of a ventricular arrhythmia requiring therapy.

Thereafter, at step S130, it is checked whether the respiratory measure corresponding to a change of rate of change of the at least one respiratory parameter satisfies predetermined at least one respiratory parameter criterion. According to this embodiment, the respiratory parameter determining circuit 52 sets the respiratory measure to a linear combination of the frequency and the tidal volume estimate. Assigning different weights to the frequency and the tidal volume estimate, the importance of them can be different. Thus, if it is seen that the respiratory frequency changes more often as a cause of a VT requiring therapy than does the tidal volume, the respiratory frequency would have a higher weight than the tidal volume. In this embodiment, the at least one respiratory parameter criterion is found to be satisfied if the respiratory measure exceeds a predetermined limit. If the respiratory parameter criterion is not satisfied, the procedure proceeds to step S140 where the detected arrhythmia is classified as an arrhythmia that do not require therapy. Optionally, the patient may be informed of this event and/or a physician of the patient. For example, an information message may be sent from the arrhythmia classifying circuit 54 via the communication circuit 57. Thereafter, the procedure returns to step S100. On the other hand, if the predetermined limit is exceeded, the procedure proceeds to step S150 where the detected arrhythmias is classified as an arrhythmias requiring therapy. Optionally, the patient may be informed of this event and/or a physician of the patient. For example, an information message may be sent from the arrhythmia classifying circuit 54 via the communication circuit 57.

In one embodiment, the arrhythmia classifying circuit 54 is adapted to classify an arrhythmia event that satisfies at least a first criterion as an arrhythmia event requiring shock treatment, to classify an arrhythmia event that satisfies at least a second criterion as an arrhythmia event requiring anti-arrhythmia pacing (ATP), and to classify an arrhythmia event that satisfied at least a third criterion as an arrhythmia event that do not require any therapy. For example, the first criterion is the predetermined limit which in this embodiment corresponds to a significant impact on the respiration, i.e. a sudden increase of the rate of change of the respiratory frequency and/or tidal volume being above a predetermine limit, and an IEGM based determination that indicates that the arrhythmia event is a ventricular tachycardia (VT) or ventricular fibrillation (VF). Further, the second criterion may include a small (or in certain cases no) impact on the respiration, i.e. an increase of the rate of change of the respiratory frequency and/or tidal volume being above a lower predetermine limit but below the predetermined limit indicating shock therapy, and an IEGM based determination that indicates that the arrhythmia event is a ventricular tachycardia (VT). A third criterion may include no impact on the respiration, i.e. an increase of the rate of change of the respiratory frequency and/or tidal volume being below the lower predetermine limit indicating ATP, and, optionally, a determination that the activity level has changed.

Figure 4:
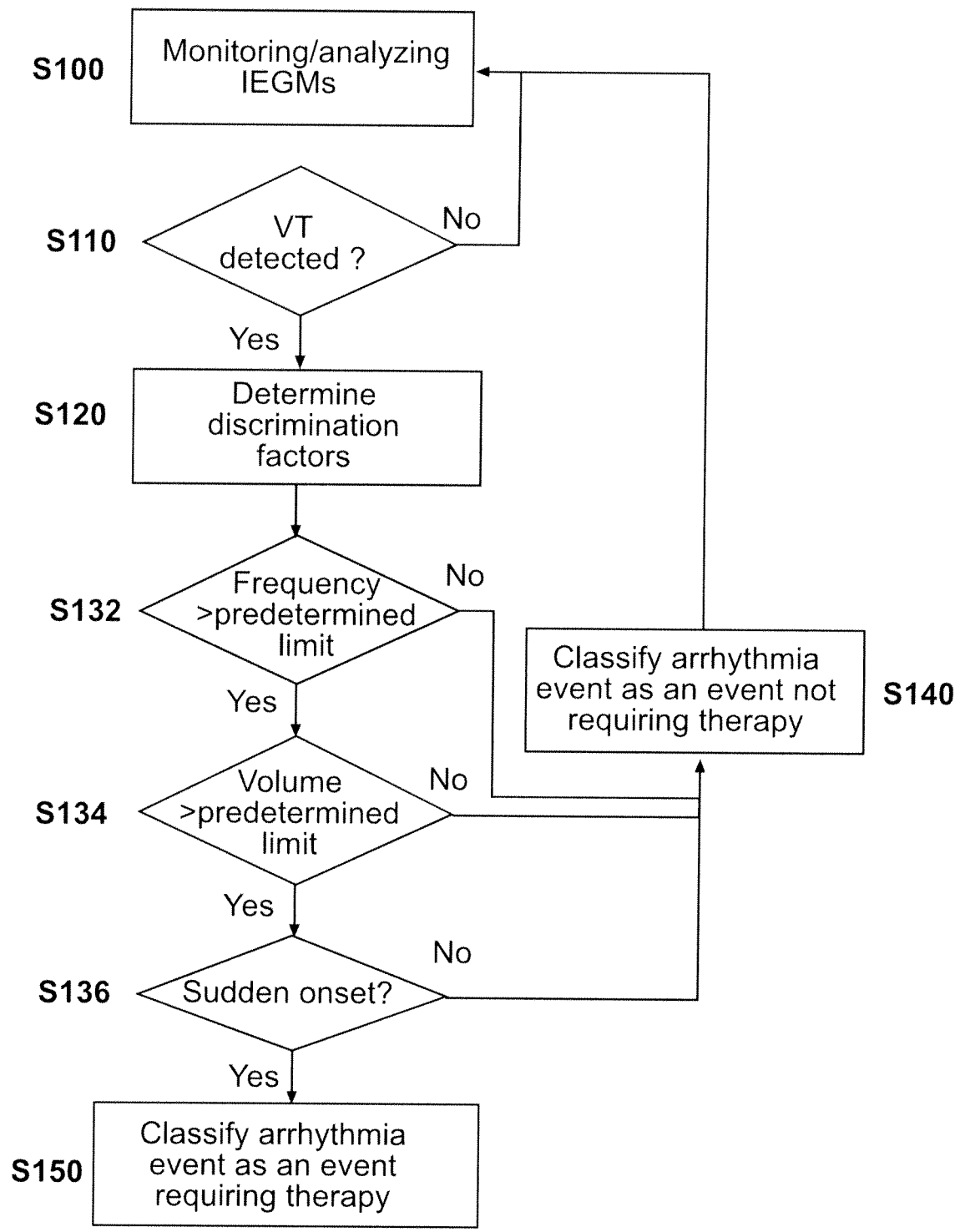
FIG. 4 is a flow chart describing another embodiment of the method according to the present invention.

In an alternative embodiment, see FIG. 4 (where similar functions are indicated with the same reference numerals), a first check is made in step S132 whether the respiratory frequency exceeds a predetermined limit, i.e. whether the frequency has increased. If no, the procedure proceeds to step S140 where the detected arrhythmia is classified as an arrhythmia that do not require therapy. Thereafter the procedure returns to step S100. However, if the respiratory frequency exceeds the predetermined limit, the procedure proceeds to step S134 where it is checked whether the tidal volume exceeds a predetermined limit, i.e. whether the volume has increased. If no, the procedure proceeds to step S140 where the detected arrhythmia is classified as an arrhythmia that do not require therapy. Thereafter the procedure returns to step S100. If the tidal volume also has increased, the procedure proceeds to step S136 where it is checked whether the increase of the tidal volume and respiratory frequency is sudden, i.e. whether the change of a rate of changes exceed predetermined limits. Alternative, the product of the two parameters can be calculated, which gives a value that correlates to the minute ventilation which represents the amount of oxygen delivered to the body per minute, and the rate of change of the product may be compared to the predetermined limit. If no, the procedure proceeds to step S140 where the detected arrhythmia is classified as an arrhythmia that do not require therapy. Thereafter the procedure returns to step S100. On the other hand, if the predetermined limit is exceeded, the procedure proceeds to step S150 where the detected arrhythmias is classified as an arrhythmias requiring therapy. In one embodiment, the arrhythmia classifying circuit 54 is adapted to classify an arrhythmia event that satisfies at least a first criterion as an arrhythmia event requiring shock treatment, and to classify an arrhythmia event that satisfies at least a second criterion as an arrhythmia event requiring anti-arrhythmia pacing (ATP). For example, the criterions may be the same as discussed above.

Figure 5:
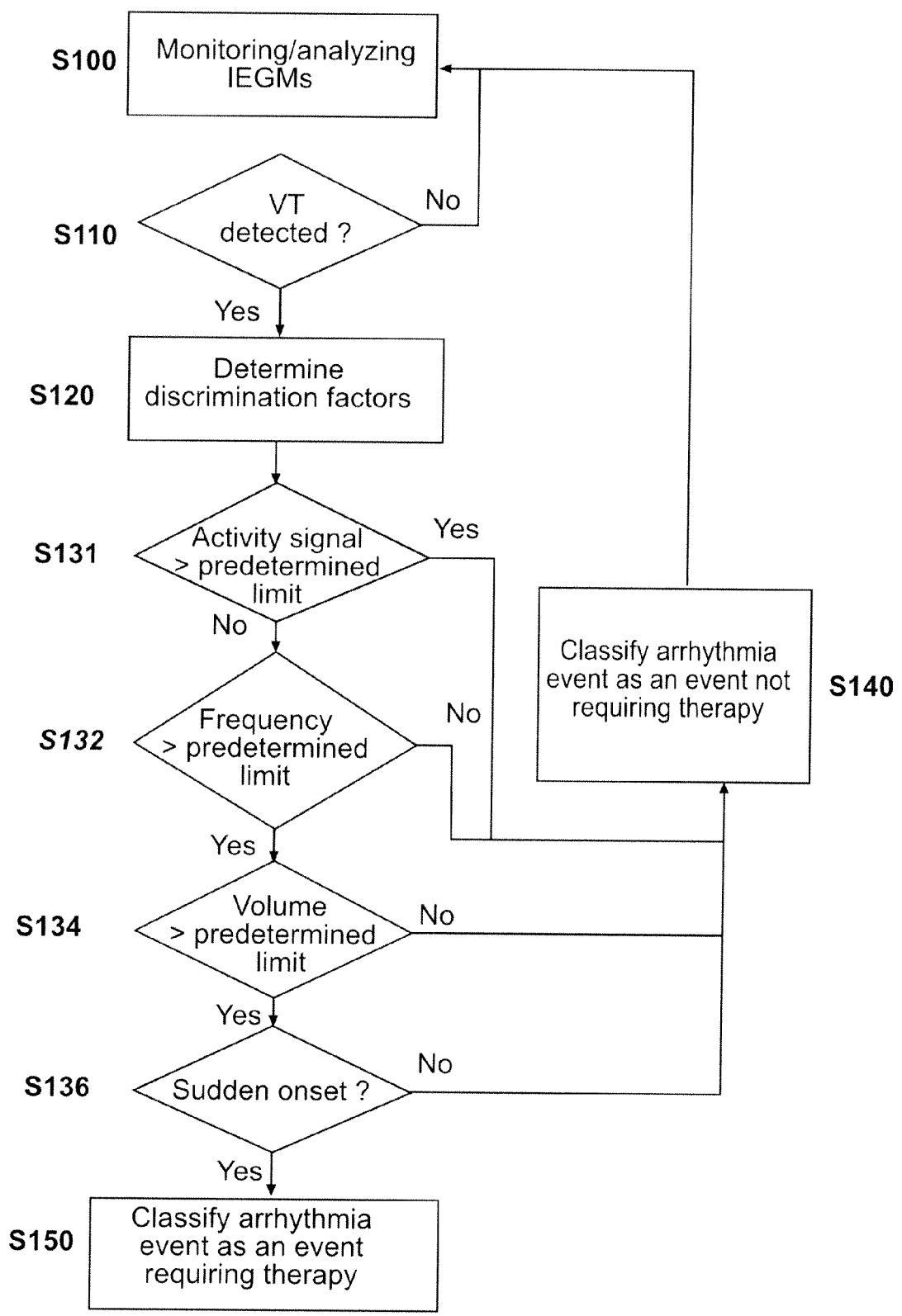
FIG. 5 is a flow chart describing a further embodiment of the method according to the present invention.

In a further embodiment, see FIG. 5 (where similar functions are indicated with the same reference numerals), a first check is made in step S131 whether an activity signal is above a first predetermined activity limit. If yes, the procedure proceeds to step S140 where the detected arrhythmia is classified as an arrhythmia that do not require therapy. Thereafter the procedure returns to step S100. However, if the activity level of the patient is below the predetermined limit, the procedure proceeds to step S132, where it is checked whether the respiratory frequency exceeds a predetermined limit, i.e. whether the frequency has increased. If no, the procedure proceeds to step S140 where the detected arrhythmia is classified as an arrhythmia that do not require therapy. Thereafter the procedure returns to step S100. However, if the respiratory frequency exceeds the predetermined limit, the procedure proceeds to step S134, where it is checked whether the tidal volume exceeds a predetermined limit, i.e. whether the volume has increased. If no, the procedure proceeds to step S140 where the detected arrhythmia is classified as an arrhythmia that do not require therapy.

Thereafter the procedure returns to step S100. If the tidal volume also has increased, the procedure proceeds to step S136 where it is checked whether the increase of the tidal volume and respiratory frequency is sudden, i.e. whether the change of a rate of changes exceed predetermined limits. Alternative, the product of the two parameters can be calculated, which gives a value that correlates to the minute ventilation which represents the amount of oxygen delivered to the body per minute, and the rate of change of the product may be compared to the predetermined limit. If no, the procedure proceeds to step S140 where the detected arrhythmia is classified as an arrhythmia that do not require therapy. Thereafter the procedure returns to step S100. On the other hand, if the predetermined limit is exceeded, the procedure proceeds to step S150 where the detected arrhythmias is classified as an arrhythmias requiring therapy. In one embodiment, the arrhythmia classifying circuit 54 is adapted to classify an arrhythmia event that satisfies at least a first criterion as an arrhythmia event requiring shock treatment, and to classify an arrhythmia event that satisfies at least a second criterion as an arrhythmia event requiring anti-arrhythmia pacing (ATP). For example, the first criterion is the predetermined limit which in this embodiment corresponds to a significant impact on the respiration, i.e. a sudden increase of the rate of change of the respiratory frequency and/or tidal volume being above a predetermine limit, and an IEGM based determination that indicates that the arrhythmia event is a ventricular tachycardia (VT) or ventricular fibrillation (VF). Further, the second criterion may include a small (or in certain cases no) impact on the respiration, i.e. an increase of the rate of change of the respiratory frequency and/or tidal volume being above a lower predetermine limit but below the predetermined limit indicating shock therapy, and an IEGM based determination that indicates that the arrhythmia event is a ventricular tachycardia (VT).

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable medical device to discriminate between ventricular tachycardias (VTs) and supraventricular tachycardias (SVTs), said implantable medical device being configured to be connected to at least one medical lead adapted to be placed at or within a heart of a patient, said medical lead including at least one electrode adapted to sense electrical activity of said heart and to produce at least one signal representative of said electrical activity, said implantable medical device comprising:
    an intra-cardiac electrogram (IEGM) analyzing circuit that receives said signal representative of said electrical activity and to analyse IEGMs of said heart to detect an arrhythmia event;
    a sensing circuit that senses a respiratory pattern of said patient and to produce at least one signal representative of said respiratory pattern;
    a respiratory parameter determining circuit that determines at least one respiratory parameter reflecting characteristics of the respiratory pattern of said patient based on said sensed respiratory pattern and that determines a respiratory measure corresponding to a change of a rate of change of said at least one respiratory parameter; and
    an arrhythmia classifying circuit that classifies the detected arrhythmia event as a VT or SVT based on said respiratory measure, including classifying arrhythmia events that satisfy at least a first criterion for VT as an arrhythmia event requiring therapy;
    wherein said respiratory parameter determining circuit determines a respiratory frequency and a tidal volume using said sensed respiratory pattern and that determines a change of a range of change of a weighted combination of said respiratory frequency and said tidal volume.

2. The implantable medical device according to claim 1, wherein said arrhythmia classifying circuit determines said at least first criterion to be satisfied when said respiratory measure is higher than a predetermined threshold value.

3. The implantable medical device according to claim 2, wherein said arrhythmia classifying circuit is configured to:
    upon receiving information from said arrhythmia detection circuit that an arrhythmia event has been detected, monitor said respiratory measure;
    compare the time points of the respective onset of said detected arrhythmia event and of a respiratory measure being higher than said predetermined threshold; and
    determine said at least first criterion to be satisfied if said respiratory measure is higher than a predetermined threshold value and an onset of said change occur within a predetermined period of time from the onset of said detected arrhythmia event.

4. The implantable medical device according to claim 1, further comprising:
    an impedance measuring circuit that, during impedance measuring sessions, measures at least one impedance signal between at least a first pair of electrodes being configured to be connected to said implantable medical device, said electrodes being located such that measured impedance signals substantially reflects the respiratory pattern of said patient; and
    wherein said respiratory parameter determining circuit determines said at least one respiratory parameter based on said measured impedance signals.

5. The implantable medical device according to claim 1, further comprising:
    an activity sensor that senses a level of physiological activity of said patient and that produces a signal representative of a current status of said physiological activity of said patient; and
    wherein said arrhythmia classifying circuit determines that said at least one first criterion is not satisfied when an activity level of said patient is above a predetermined level.

6. The implantable medical device according to claim 1, wherein said arrhythmia classifying circuit classifies an arrhythmia event that satisfies at least said first criterion as an arrhythmia event requiring shock treatment and classifies an arrhythmia event that satisfies at least a second criterion an arrhythmia event requiring anti-arrhythmia pacing.

7. A method to discriminate between ventricular tachycardias (VTs) and supraventricular tachycardias (SVTs) in an implantable medical device, the implantable medical device being configured to be connected to at least one medical lead adapted to be placed at or within a heart of a patient, said medical lead including at least one electrode adapted to sense electrical activity of said heart and to produce at least one signal representative of said electrical activity, wherein said method comprises:
    analyzing IEGMs of said heart to detect an arrhythmia event;
    sensing a respiratory pattern of said patient producing at least one signal representative of said respiratory pattern;
    determining at least on respiratory parameter reflecting characteristics of the respiratory pattern of said patient based on said sensed respiratory pattern;
    determining a respiratory measure corresponding to a change of a rate of change of said at least on respiratory parameter; and
    classifying the detected arrhythmia event as a VT or SVT based on said respiratory measure, wherein arrhythmia events that satisfy at least a first criterion for VT is classified as an arrhythmia event requiring therapy;
    wherein said determining at least one respiratory parameter reflecting comprises determining a respiratory frequency and a tidal volume using said sensed respiratory pattern and wherein said determining a respiratory measure comprises determining a change of a rate of change of a weighted combination of said respiratory frequency and said tidal volume.

8. The method according to claim 7, wherein said classifying comprises: determining said at least first criterion to be satisfied when said respiratory measure is higher than a predetermined threshold value.

9. The method according to claim 8, wherein said classifying further comprises;
    upon receiving information from said arrhythmia detection circuit that an arrhythmia event has been detected, monitoring said respiratory measure;
    comparing the time points for the respective onset of said detected arrhythmia event and of a respiratory measure being higher than said predetermined threshold; and
    determining said at least first criterion for VT to be satisfied if said respiratory measure is higher than a predetermined threshold value and an onset of said change occur within a predetermined period of time from the onset of said detected arrhythmia event.

10. The method according to claim 7, further comprising, during impedance measuring sessions, measuring at least one impedance signal between at least a first pair of electrodes configured to be connected to said implantable medical device, said electrodes being located such that measured impedance signals substantially reflects the respiratory pattern of said patient; and wherein said determining said respiratory parameter includes determining said at least one respiratory parameter based on said measured impedance signals.

11. The method according to claim 7, further comprising:
sensing a level of physiological activity of said patient; and
wherein said classifying comprises determining that said at least one first criterion for VT is not satisfied if an activity level of said patient is above a predetermined level.

12. The method according to claim 7, wherein said classifying further comprises:
classifying an arrhythmia event that satisfies at least said first criterion for VT as an arrhythmia event requiring shock treatment; and
classifying an arrhythmia event that satisfies at least a second criterion for SVT as an arrhythmia event requiring anti-arrhythmia pacing.

* * * * *